United States Patent
Ter Riet et al.

(10) Patent No.: US 12,173,303 B2
(45) Date of Patent: Dec. 24, 2024

(54) LETTUCE PLANT RESISTANT TO DOWNY MILDEW AND RESISTANCE GENE

(71) Applicant: Enza Zaden Beheer B.V., Enkhuizen (NL)

(72) Inventors: Bas Ter Riet, Enkhuizen (NL); Mathieu Andre Pel, Enkhuizen (NL); Stephanie Melanie Broos, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 505 days.

(21) Appl. No.: 17/414,142

(22) PCT Filed: Dec. 4, 2019

(86) PCT No.: PCT/EP2019/083651
§ 371 (c)(1),
(2) Date: Jun. 15, 2021

(87) PCT Pub. No.: WO2020/126500
PCT Pub. Date: Jun. 25, 2020

(65) Prior Publication Data
US 2022/0090119 A1    Mar. 24, 2022

(30) Foreign Application Priority Data

Dec. 17, 2018    (WO) .................. PCT/EP2018/085244

(51) Int. Cl.
*C12N 15/82*    (2006.01)
(52) U.S. Cl.
CPC .............................. *C12N 15/8282* (2013.01)

(58) Field of Classification Search
None
See application file for complete search history.

(56) References Cited

U.S. PATENT DOCUMENTS

| 6,350,933 B1 | 2/2002 | Michelmore et al. |
| 2020/0000054 A1 | 1/2020 | Jeuken et al. |

FOREIGN PATENT DOCUMENTS

| WO | 9830083 A1 | 7/1998 |
| WO | 2015136085 A1 | 9/2015 |

OTHER PUBLICATIONS

Brown et al. "Plant regeneration from protoplasts of a wild lettuce species (*Lactuca saligna* L.)" 1987 Plant Cell Reports 6:180-182. (Year: 1987).*
Den Boer 2014 PhD Thesis ("Genetic investigation of the nonhost resistance of wild lettuce, *Lactuca saligna*, to lettuce downy mildew, *Bremia lactucae*" to Wageningen University, 186 total pages). (Year: 2014).*

(Continued)

*Primary Examiner* — Matthew R Keogh
*Assistant Examiner* — Rebecca Stephens
(74) *Attorney, Agent, or Firm* — The Webb Law Firm

(57) ABSTRACT

Provided herein is a lettuce plant that is resistant to downy mildew, more specifically a lettuce plant that includes a mutated gene that confers broad spectrum resistance to oomycetes in lettuce, more specifically *Bremia lactucae*. Furthermore also provided herein are a resistance gene and a method for obtaining a lettuce plant that is resistant to downy mildew, wherein the method includes the step of mutating a gene.

14 Claims, 9 Drawing Sheets

Specification includes a Sequence Listing.

|  | Bl:16 | Bl:17 | Bl:18 | Bl:19 | Bl:20 | Bl:21 | Bl:22 | Bl:23 | Bl:24 | Bl:25 |
|---|---|---|---|---|---|---|---|---|---|---|
| Cobham Green | + | + | + | + | + | + | + | + | + | + |
| Green Towers | + | + | + | + | + | + | + | + | + | + |
| Vanity | + | + | + | + | + | + | + | + | + | + |
| SL7R | + | - | - | ND | + | + | - | + | - | - |

|  | Bl:26 | Bl:27 | Bl:28 | Bl:29 | Bl:30 | Bl:31 | Bl:32 | Bl:33 | Bl:34 | Bl:35 |
|---|---|---|---|---|---|---|---|---|---|---|
| Cobham Green | + | + | + | + | + | + | + | + | ND | ND |
| Green Towers | + | + | + | + | + | + | + | + | ND | ND |
| Vanity | + | + | + | + | + | + | + | + | + | + |
| SL7R | - | + | - | - | - | - | - | - | - | - |

(56) References Cited

OTHER PUBLICATIONS

Database GenBank—Nucleotide [Online] NCBI, "Predicted: Lactuca sativa putative disease resistance protein At3g14460 (LOC111918844), partial mRNA," 2018, XP002793007, Database accession No. PLY80533.
Database EMBL [Online], "Lactuca sativa hypothetical protein," 2018, XP002793008, Database accession No. PLY80533.
Huang et al. Virus-induced gene silencing and its application in plant functional genomics. Sci China Life Sci 2012, pp. 99-108, vol. 55, No. 2.
Parra et al., "Rationalization of genes for resistance to Bremia lactucae in lettuce," Euphytica, 2016, pp. 309-326, 210.

* cited by examiner

Figure 4

|              | Bl:16 | Bl:17 | Bl:18 | Bl:19 | Bl:20 | Bl:21 | Bl:22 | Bl:23 | Bl:24 | Bl:25 |
|--------------|-------|-------|-------|-------|-------|-------|-------|-------|-------|-------|
| Cobham Green | +     | +     | +     | +     | +     | +     | +     | +     | +     | +     |
| Green Towers | +     | +     | +     | +     | +     | +     | +     | +     | +     | +     |
| Vanity       | +     | +     | +     | +     | +     | +     | +     | +     | +     | +     |
| SL7R         | +     | -     | -     | ND    | +     | +     | -     | +     | -     | -     |

|              | Bl:26 | Bl:27 | Bl:28 | Bl:29 | Bl:30 | Bl:31 | Bl:32 | Bl:33 | Bl:34 | Bl:35 |
|--------------|-------|-------|-------|-------|-------|-------|-------|-------|-------|-------|
| Cobham Green | +     | +     | +     | +     | +     | +     | +     | +     | ND    | ND    |
| Green Towers | +     | +     | +     | +     | +     | +     | +     | +     | ND    | ND    |
| Vanity       | +     | +     | +     | +     | +     | +     | +     | +     | +     | +     |
| SL7R         | -     | +     | -     | -     | -     | -     | -     | -     | -     | -     |

Figure 5

```
        1                   20                    40                    60
        |                   |                     |                     |
SL7     MPVGMIESWTTFYLSNKVLDDLLHELPLLRVLSLSHISKEVPEIIGSLKHLRYLNLSHTTTHLPENICNLYNL
SL7R    MPVGMIESWTRFYLSNKVLDDLLHELPLLRVLSLSHINTEVPEIIQNLKHLRYLNLSHTSITHLPENVCNLYNL 80                  100                   120                   140
            |                   |                     |                     |
SL7     QTLILCGCCFITKFEDNFLKLRNLRHLDISDTPGLKKMSSGIGELKNLHTLSKVIIGGENRLNELKNLQNLHGKI
SL7R    QTLILCGGRFITKFENNFLKLRNLRHLDISDTPGLKKMSSGIGELKNLHTLSKIIIGGENRLNELKNLQNLHGKI
```

Figure 6 cDNA sequence *SL7 Lactuca sativa* (SEQ ID No.1):

ATGCCTGTTGGGATGATAGAAAGTTGGACAACATTTTACTTATCAAATAAGGTCCTCGATGA
CTTACTTCATGAGTTACCATTGTTGAGAGTTCTAAGTTTGAGTCATCTTAGCATCAAGGAGGT
ACCTGAAATAATAGGCAGTTTGAAACACTTGCGGTATCTTAATTTATCACACACTACCATCA
CACATTTACCGGAAAATATATGCAATCTTTACAACTTACAGACATTGATCCTTTGTGGCTGTT
GTTTTATAACCAAGTTTCCCGACAACTTCTTAAAGCTTAGAAATTTACGGCATTTGGACATTA
GCGATACTCCCGGTTTGAAGAAGATGTCCTCGGGGATTGGTGAATTGAAGAACCTACACACT
CTCTCCAAGGTCATTATTGGAGGTGAAAATAGACTAAACGAGCTTAAGAACTTGCAAAATCT
CCATGGGAAAATTTCCGTTTGGGGGTTGGGCGATGTGCAAAATGCAATGGAGGCACGTGAG
GCGAATTTATCACAAAAGAAACTTAGCGAGTTACAGTTGGATTGGGGTTATGGGGATTATGG
GTTGAATGTTTCTCGAAAGCAAACCCATGATAAGGAGGTCCTTAATGAGCTGAAGCCTGATA
ACGATAGTTTGAAAAAGCTTGAAATTTTGTCATATGGAGGTACAGAGTTTCCAAATTGGGTT
GGGAATCCCTCGTTTCTTATACTAACTCATGTGTCCATAAATTTCTGTGAAGAATGTACATGT
CTACCAAGTCTTGGGAAGTTACCATCACTTAAGGAGCTGTTTATTCTTGGCATGAGCAAGGT
GAAAGTTATTGATTTGGAGTTACTTGGAACTGGAGTTGCATTCCCATCACTTGAATTCTAA
GTTTTCGTCATATGTCAGGGTGGGAGGTATGGTCAACTGATAATGGTGGGGTTGTAGACACA
GCATTTCCATGTCTTCAAGAACTTCATATCGAATTTTGTCCTAATTTAGTTCAAGTCTCACTT
GAAGCCCTACCTTCACTTAGAGTTTTAGAAATAAAAGGATGTGGTCATGGTGTGTTGACAAC
TCTGCTTCATGTAGCTTCTTCAGTCACCATGTTGGAAATAGATAATATTTCAGGGCTTACTGA
TGAACTGTGGAGAAGTGTTTTCAAGTATCTTGGGAAACTTGAAAAGTTATACATTAGTGGGT
GTAATGAAATAAGATATTTGTGGCAATCAGAAGTAGAGGCAAGTAAGTCTCTAGTGAATTTA
AGGAATTTGAATGTGAGTGCTTGTTCAAATCTGGTGGGTTTAGGAGAGAAAGTGGAGGATA
ACTGTGGAAGCATCCAGACGTTTATTAGGATGTTGTCTATAGCACGTTGTGAGAGTATTGAG
CATTGCAGTTGTCCTAATAGCATTGAGTTTCTGAATATCCATGATTGTGATTCAATTACATCA
GTGTCTTTCCCAACTGGAGGAGGGAAGAAGCTCAAGTCATTTGCAATTGAAGGTTGTCAGAA
GTTTTTGGAAGAGGACCTTGGAGGAGAAAAGAGTAGGTTGCTTATCAAATCAAGCATGCAA
ATGCTTGAATCTGTAGATATAAATGGTTGGGTAAATCTGAAATCTATCATTGAATTAAGTTA
CTGTATTCACCTCACCACATTGATGATAACAAAGTGTCCAAAAATGGAGTCGTTTCCCGACC
ATGAGTTACCCAATCTCACCTCTTTAACAATTCTGGTAATAGCAAAGTGTCCAAGTATTGAT
GCCTCCTTTCCTCGTGGGCTTTGGCCTCCCAAATTGAGTTACCTTGGAATAGGAGGATTGAA
GAAGCCCATCTCAGAGTGGGGCCCACAGAATTTCCCAACCTCACTCGAGAACTTGATGTTAA
ATGGCGGAATATATGATGATGTGAAAAACTTTGATCAATTGTCGCATCTTTTCCTTCATCTC
TTGCTTCTCTTTCGATAATGGGATTTCAGAAACTGGAATCAGTTTCAATGGGACTCCAAAAC
CTCACCTTTCTCCAGCGTCTCTTTGTTTCCAAGTGCCCGAAGATGTTACATCTACCAGAAAAG
TTGTTTCCTTCGCTTTTGTCTTTGAGAATCGATGGATGCCCAAATTTGAATGAAAGGAGCATT
AGAAGAAGCTCCTATTGGCCCCTCATCTCCCTTATCCCAGACTCCACTTTTGACGAGTAA

Figure 7

Protein sequence *SL7, Lactuca sativa* (SEQ ID No.2):

MPVGMIESWTTFYLSNKVLDDLLHELPLLRVLSLSHLSIKEVPEIIGSLKHLRYLNLSHTTITHLPE
NICNLYNLQTLILCGCCFITKFPDNFLKLRNLRHLDISDTPGLKKMSSGIGELKNLHTLSKVIIGGE
NRLNELKNLQNLHGKISVWGLGDVQNAMEAREANLSQKKLSELQLDWGYGDYGLNVSRKQTH
DKEVLNELKPDNDSLKKLEILSYGGTEFPNWVGNPSFLILTHVSINFCEECTCLPSLGKLPSLKELF
ILGMSKVKVIDLELLGTGVAFPSLEILSFRHMSGWEVWSTDNGGVVDTAFPCLQELHIEFCPNLV
QVSLEALPSLRVLEIKGCGHGVLTTLLHVASSVTMLEIDNISGLTDELWRSVFKYLGKLEKLYISG
CNEIRYLWQSEVEASKSLVNLRNLNVSACSNLVGLGEKVEDNCGSIQTFIRMLSIARCESIEHCSC
PNSIEFLNIHDCDSITSVSFPTGGGKKLKSFAIEGCQKFLEEDLGGEKSRLLIKSSMQMLESVDING
WVNLKSIIELSYCIHLTTLMITKCPKMESFPDHELPNLTSLTILVIAKCPSIDASFPRGLWPPKLSYL
GIGGLKKPISEWGPQNFPTSLENLMLNGGIYDDVKNFDQLSHLFPSSLASLSIMGFQKLESVSMGL
QNLTFLQRLFVSKCPKMLHLPEKLFPSLLSLRIDGCPNLNERSIRRSSYWPLISLIPDSTFDE

Figure 8 cDNA sequence *SL7R, Lactuca saligna* (SEQ ID No.3):

ATGCCTGTTGGGATGATAGAAAGTTGGACAAGATTTTACTTATCAAATAAGGTCCTGGATGA
CTTACTTCACGAGTTACCATTGTTGAGAGTTCTAAGTTTGAGTCATCTTAACATCACAGAGGT
ACCTGAAATAATAGGCAATTTGAAACACTTGCGGTATCTTAATTTATCTCACACGAGTATCA
CACATTTACCAGAAAATGTCTGCAATCTTTACAACTTACAAACATTGATCCTTTGTGGCTGTC
GTTTTATAACCAAGTTTCCCAACAACTTCTTAAAGCTTAGAAATTTACGGCATTTGGACATTA
GCGATACTCCCGGTTTGAAGAAGATGTCCTCGGGGATTGGTGAATTGAAGAACCTACACACT
CTCTCCAAGATCATTATTGGAGGTGAAAATAGACTAAACGAGCTTAAGAACTTACAAAATCT
CCATGGGAAAATTTCCGTTTGGGGGTTGGGCGATGTGCAAAATGCAATGGAGGCACGTGAG
GCGAATTTATCACAAAAGAAACTTGGCGAGTTACAGTTGGATTGGGGTTATGGGGATTATGA
GTTGAATGTTTCTCGAAAGCAAACCCATGATAAGGAGGTCCTTAATGAGCTGAAGCCTGATA
ACGATAGTTTGAAAAAGCTTAAAATTTTGTCATATGGAGGTACAGAGTTTCCAAATTGGGTT
GGGAGTCCCTCGTTTCTTATGCTAACTCATGTGTCCATATATTTCTGTGAAGAATGTACATAT
CTACCAAGTCTTGGGAAGTTACCATCACTTAAGGAGCTGTTTATTCTTGGCATGAGCAAGGT
GAAAGTTATTGATTGGGAGTTACTTGGAACTGGAGTTGCATTCCCATCACTTGAAATTCTAA
GTTTTGGTCATATGTCAGGGTGGGAGGTATGGTCAACCGAGAATAGTGGGGTTGTAGACACA
GCATTTCCATGTCTTCAAGAACTTCATATCGAATTTTGTCCTAATTTAGTTCAAGTCTCACTT
GAAGCCCTACCTTCACTTAGAGTTTTAGAAATAAAAGGATGTGGTCATGGTGTGTTGACAAC
TCTGGTTCATGTAGCTTCTTCAGTCACCATGTTGGAAATAGGTAATATTTCAGGGCTTAATGA
TGAACTGTGGAGAAGTGCTTTCAAGTATCTTGGGAAACTTGAAAAGTTATACATTCGTGGGT
GTAATGAAATAAGATATTTGTGGCAATCAGAAGTAGAGGCAAGTAAGTCTCTAGTGAATTTA
AGGAATTTGGATGTGAGTGATTGTTCAAATCTGGTGGGTTTAGGAGAGAAAGTGGAGGATA
ACTCTGGAAGCATCCAGACGTTTATTAGGATGTTGTCTATAGCACGTTGTGAGACTATTGAG
CATTGCAGTTGTCCTAATAGCATTGAGTTTCTGAATATCCATGATTGTGATTCAATTACATCA
GTGTCTTTCCCAAAAGGAGGAGGGAAGAAGCTCAAGTCATTTGCCATTGAAGGTTGTCAGA
AGTTTTTGGAAGAGGAGCTCGGAGGAGAAAAGAGTAGGTTGCTTATCAACTCAAACATGAA
AATGCTTGAATCTGTAGATATAAATGGTTGGGTAAATCTGAAATCTATCATTGAATTGAGTT
ACTGTATTCACCTCACCACATTGATGATAACAAAGTGTCCAAAAATGGAGTCTTTTCCTGAC
CATGAGTTACCCAATCTCACCTCTTTAACAATTCTGATAATAGCAAAGTGTCCAAGTATTGAT
GCCTCCTTTCCTCGTGGGCTTTGGCCTCCCAAATTGAGTTACCTTGGAATAGGAGGATTGAA
GAAGCCCATCTCAGAGTGGGGCCCACAGAATTTCCCAACCTCACTCGAGCACTTAATGTTAA
ATGGCGGAATATATGATGATGTGAAAAACTTTGATCAATTGTCGCATCTTTTCCTTCATCTC
TTGCTTCTCTTTCGATAACGGGATTTCAGAAACTTGAATCAGTTTCATTGGGACTCCAAAACC
TCACCTTTCTCCAGCGTCTCTCTGTTTCCAAGTGCCCAAAGATGTTACATCTACCAGAAAAGT
TGCTTCCTTCGCTTTTGTCTTTGAGTATCGATAGATGCCCAAATTTGAATAAAAGGAGCATTA
GAAGAAGCTCCTATTGGCCCCTCATCTCCCTTATCCCAGACTCTAGGTATGCCCCTCTCAAAG
TTTTTGACTTCTTCTAG

Figure 9

Protein sequence *SL7R, Lactuca saligna* (SEQ ID No.4):

MPVGMIESWTRFYLSNKVLDDLLHELPLLRVLSLSHLNITEVPEIIGNLKHLRYLNLSHTSITHLPE
NVCNLYNLQTLILCGCRFITKFPNNFLKLRNLRHLDISDTPGLKKMSSGIGELKNLHTLSKIIIGGE
NRLNELKNLQNLHGKISVWGLGDVQNAMEAREANLSQKKLGELQLDWGYGDYELNVSRKQT
HDKEVLNELKPDNDSLKKLKILSYGGTEFPNWVGSPSFLMLTHVSIYFCEECTYLPSLGKLPSLKE
LFILGMSKVKVIDWELLGTGVAFPSLEILSFGHMSGWEVWSTENSGVVDTAFPCLQELHIEFCPN
LVQVSLEALPSLRVLEIKGCGHGVLTTLVHVASSVTMLEIGNISGLNDELWRSAFKYLGKLEKLY
IRGCNEIRYLWQSEVEASKSLVNLRNLDVSDCSNLVGLGEKVEDNSGSIQTFIRMLSIARCETIEH
CSCPNSIEFLNIHDCDSITSVSFPKGGGKKLKSFAIEGCQKFLEEELGGEKSRLLINSNMKMLESVD
INGWVNLKSIIELSYCIHLTTLMITKCPKMESFPDHELPNLTSLTILIIAKCPSIDASFPRGLWPPKLS
YLGIGGLKKPISEWGPQNFPTSLEHLMLNGGIYDDVKNFDQLSHLFPSSLASLSITGFQKLESVSL
GLQNLTFLQRLSVSKCPKMLHLPEKLLPSLLSLSIDRCPNLNKRSIRRSSYWPLISLIPDSRYAPLK
VFDFF

SEQUENCE LISTING

```
<160> NUMBER OF SEQ ID NOS: 16

<210> SEQ ID NO 1
<211> LENGTH: 2175
<212> TYPE: DNA
<213> ORGANISM: Lactuca sativa

<400> SEQUENCE: 1
atgcctgttg ggatgataga aagttggaca acattttact tatcaaataa ggtcctcgat      60
gacttacttc atgagttacc attgttgaga gttctaagtt tgagtcatct tagcatcaag     120
gaggtacctg aaataatagg cagtttgaaa cacttgcggt atcttaattt atcacacact     180
accatcacac atttaccgga aaatatatgc aatctttaca acttacagac attgatcctt     240
tgtggctgtt gttttataac caagtttccc gacaacttct taaagcttag aaatttacgg     300
catttggaca ttagcgatac tcccggtttg aagaagatgt cctcggggat tggtgaattg     360
aagaacctac acactctctc caaggtcatt attggaggtg aaaatagact aaacgagctt     420
aagaacttgc aaaatctcca tgggaaaatt tccgtttggg ggttgggcga tgtgcaaaat     480
gcaatggagg cacgtgaggc gaatttatca caaaagaaac ttagcgagtt acagttggat     540
tggggttatg gggattatgg gttgaatgtt tctcgaaagc aaacccatga taaggaggtc     600
cttaatgagc tgaagcctga taacgatagt ttgaaaaagc ttgaaatttt gtcatatgga     660
ggtacagagt ttccaaattg ggttgggaat ccctcgtttc ttatactaac tcatgtgtcc     720
ataaatttct gtgaagaatg tacatgtcta ccaagtcttg ggaagttacc atcacttaag     780
gagctgttta ttcttggcat gagcaaggtg aaagttattg atttggagtt acttggaact     840
ggagttgcat tcccatcact tgaaattcta agttttcgtc atatgtcagg gtgggaggta     900
tggtcaactg ataatggtgg ggttgtagac acagcatttc catgtcttca agaacttcat     960
atcgaatttt gtcctaattt agttcaagtc tcacttgaag ccctaccttc acttagagtt    1020
ttagaaataa aaggatgtgg tcatggtgtg ttgacaactc tgcttcatgt agcttcttca    1080
gtcaccatgt tggaaataga taatatttca gggcttactg atgaactgtg gagaagtgtt    1140
ttcaagtatc ttgggaaact tgaaaagtta tacattagtg ggtgtaatga aataagatat    1200
ttgtggcaat cagaagtaga ggcaagtaag tctctagtga atttaaggaa tttgaatgtg    1260
agtgcttgtt caaatctggt gggtttagga gagaaagtgg aggataactg tggaagcatc    1320
cagacgttta ttaggatgtt gtctatagca cgttgtgaga gtattgagca ttgcagttgt    1380
cctaatagca ttgagtttct gaatatccat gattgtgatt caattacatc agtgtctttc    1440
```

```
ccaactggag gagggaagaa gctcaagtca tttgcaattg aaggttgtca gaagtttttg    1500
gaagaggacc ttggaggaga aaagagtagg ttgcttatca aatcaagcat gcaaatgctt    1560
gaatctgtag atataaatgg ttgggtaaat ctgaaatcta tcattgaatt aagttactgt    1620
attcacctca ccacattgat gataacaaag tgtccaaaaa tggagtcgtt tcccgaccat    1680
gagttaccca atctcacctc tttaacaatt ctggtaatag caaagtgtcc aagtattgat    1740
gcctcctttc ctcgtgggct ttggcctccc aaattgagtt accttggaat aggaggattg    1800
aagaagccca tctcagagtg gggcccacag aatttcccaa cctcactcga aacttgatg     1860 ttaaatggcg aatatatga tgatgtgaaa aactttgatc aattgtcgca tcttttcct     1920 tcatctcttg cttctctttc gataatggga tttcagaaac tggaatcagt ttcaatggga    1980
ctccaaaacc tcacctttct ccagcgtctc tttgtttcca agtgcccgaa gatgttacat    2040
ctaccagaaa agttgtttcc ttcgcttttg tctttgagaa tcgatggatg cccaaatttg    2100
aatgaaagga gcattagaag aagctcctat tggcccctca tctcccttat cccagactcc    2160
acttttgacg agtaa                                                     2175
```

<210> SEQ ID NO 2
<211> LENGTH: 724
<212> TYPE: PRT
<213> ORGANISM: Lactuca sativa

<400> SEQUENCE: 2

```
Met Pro Val Gly Met Ile Glu Ser Trp Thr Thr Phe Tyr Leu Ser Asn
1               5                   10                  15

Lys Val Leu Asp Asp Leu Leu His Glu Leu Pro Leu Leu Arg Val Leu
            20                  25                  30

Ser Leu Ser His Leu Ser Ile Lys Glu Val Pro Glu Ile Ile Gly Ser
        35                  40                  45

Leu Lys His Leu Arg Tyr Leu Asn Leu Ser His Thr Thr Ile Thr His
    50                  55                  60

Leu Pro Glu Asn Ile Cys Asn Leu Tyr Asn Leu Gln Thr Leu Ile Leu
65                  70                  75                  80

Cys Gly Cys Cys Phe Ile Thr Lys Phe Pro Asp Asn Phe Leu Lys Leu
                85                  90                  95

Arg Asn Leu Arg His Leu Asp Ile Ser Asp Thr Pro Gly Leu Lys Lys
            100                 105                 110

Met Ser Ser Gly Ile Gly Glu Leu Lys Asn Leu His Thr Leu Ser Lys
        115                 120                 125

Val Ile Ile Gly Gly Glu Asn Arg Leu Asn Glu Leu Lys Asn Leu Gln
    130                 135                 140

Asn Leu His Gly Lys Ile Ser Val Trp Gly Leu Gly Asp Val Gln Asn
145                 150                 155                 160

Ala Met Glu Ala Arg Glu Ala Asn Leu Ser Gln Lys Lys Leu Ser Glu
                165                 170                 175

Leu Gln Leu Asp Trp Gly Tyr Gly Asp Tyr Gly Leu Asn Val Ser Arg
            180                 185                 190

Lys Gln Thr His Asp Lys Glu Val Leu Asn Glu Leu Lys Pro Asp Asn
        195                 200                 205

Asp Ser Leu Lys Lys Leu Glu Ile Leu Ser Tyr Gly Gly Thr Glu Phe
    210                 215                 220

Pro Asn Trp Val Gly Asn Pro Ser Phe Leu Ile Leu Thr His Val Ser
225                 230                 235                 240
```

```
Ile Asn Phe Cys Glu Glu Cys Thr Cys Leu Pro Ser Leu Gly Lys Leu
                    245                 250                 255

Pro Ser Leu Lys Glu Leu Phe Ile Leu Gly Met Ser Lys Val Lys Val
            260                 265                 270

Ile Asp Leu Glu Leu Leu Gly Thr Gly Val Ala Phe Pro Ser Leu Glu
            275                 280                 285

Ile Leu Ser Phe Arg His Met Ser Gly Trp Glu Val Trp Ser Thr Asp
            290                 295                 300

Asn Gly Gly Val Val Asp Thr Ala Phe Pro Cys Leu Gln Glu Leu His
305                 310                 315                 320

Ile Glu Phe Cys Pro Asn Leu Val Gln Val Ser Leu Glu Ala Leu Pro
                325                 330                 335

Ser Leu Arg Val Leu Glu Ile Lys Gly Cys His Gly Val Leu Thr
            340                 345                 350

Thr Leu Leu His Val Ala Ser Ser Val Thr Met Leu Glu Ile Asp Asn
            355                 360                 365

Ile Ser Gly Leu Thr Asp Glu Leu Trp Arg Ser Val Phe Lys Tyr Leu
            370                 375                 380

Gly Lys Leu Glu Lys Leu Tyr Ile Ser Gly Cys Asn Glu Ile Arg Tyr
385                 390                 395                 400

Leu Trp Gln Ser Glu Val Glu Ala Ser Lys Ser Leu Val Asn Leu Arg
                405                 410                 415

Asn Leu Asn Val Ser Ala Cys Ser Asn Leu Val Gly Leu Gly Glu Lys
            420                 425                 430

Val Glu Asp Asn Cys Gly Ser Ile Gln Thr Phe Ile Arg Met Leu Ser
            435                 440                 445

Ile Ala Arg Cys Glu Ser Ile Glu His Cys Ser Cys Pro Asn Ser Ile
450                 455                 460

Glu Phe Leu Asn Ile His Asp Cys Asp Ser Ile Thr Ser Val Ser Phe
465                 470                 475                 480

Pro Thr Gly Gly Gly Lys Lys Leu Lys Ser Phe Ala Ile Glu Gly Cys
                485                 490                 495

Gln Lys Phe Leu Glu Glu Asp Leu Gly Gly Glu Lys Ser Arg Leu Leu
            500                 505                 510

Ile Lys Ser Ser Met Gln Met Leu Glu Ser Val Asp Ile Asn Gly Trp
            515                 520                 525

Val Asn Leu Lys Ser Ile Ile Glu Leu Ser Tyr Cys Ile His Leu Thr
            530                 535                 540

Thr Leu Met Ile Thr Lys Cys Pro Lys Met Glu Ser Phe Pro Asp His
545                 550                 555                 560

Glu Leu Pro Asn Leu Thr Ser Leu Thr Ile Leu Val Ile Ala Lys Cys
                565                 570                 575

Pro Ser Ile Asp Ala Ser Phe Pro Arg Gly Leu Trp Pro Pro Lys Leu
            580                 585                 590

Ser Tyr Leu Gly Ile Gly Gly Leu Lys Lys Pro Ile Ser Glu Trp Gly
            595                 600                 605

Pro Gln Asn Phe Pro Thr Ser Leu Glu Asn Leu Met Leu Asn Gly Gly
            610                 615                 620

Ile Tyr Asp Asp Val Lys Asn Phe Asp Gln Leu Ser His Leu Phe Pro
625                 630                 635                 640

Ser Ser Leu Ala Ser Leu Ser Ile Met Gly Phe Gln Lys Leu Glu Ser
                645                 650                 655

Val Ser Met Gly Leu Gln Asn Leu Thr Phe Leu Gln Arg Leu Phe Val
```

```
                    660              665               670
Ser Lys Cys Pro Lys Met Leu His Leu Pro Glu Lys Leu Phe Pro Ser
                675              680              685

Leu Leu Ser Leu Arg Ile Asp Gly Cys Pro Asn Leu Asn Glu Arg Ser
            690              695              700

Ile Arg Arg Ser Ser Tyr Trp Pro Leu Ile Ser Leu Ile Pro Asp Ser
705              710              715              720

Thr Phe Asp Glu

<210> SEQ ID NO 3
<211> LENGTH: 2196
<212> TYPE: DNA
<213> ORGANISM: Lactuca saligna

<400> SEQUENCE: 3
atgcctgttg ggatgataga aagttggaca agattttact tatcaaataa ggtcctggat    60
gacttacttc acgagttacc attgttgaga gttctaagtt tgagtcatct taacatcaca    120
gaggtacctg aaataatagg caatttgaaa cacttgcggt atcttaattt atctcacacg    180
agtatcacac atttaccaga aaatgtctgc aatctttaca acttcaaaac attgatcctt    240
tgtggctgtc gttttataac caagtttccc aacaacttct taaagcttag aaatttacgg    300
catttggaca ttagcgatac tcccggtttg aagaagatgt cctcggggat tggtgaattg    360
aagaacctac acactctctc caagatcatt attggaggtg aaaatagact aaacgagctt    420
aagaacttac aaaatctcca tgggaaaatt tccgtttggg ggttgggcga tgtgcaaaat    480
gcaatggagg cacgtgaggc gaatttatca caaaagaaac ttggcgagtt acagttggat    540
tggggttatg gggattatga gttgaatgtt ctctcgaaagc aaacccatga taaggaggtc    600
cttaatgagc tgaagcctga taacgatagt ttgaaaaagc ttaaaatttt gtcatatgga    660
ggtacagagt ttccaaattg ggttgggagt ccctcgtttc ttatgctaac tcatgtgtcc    720
atatatttct gtgaagaatg tacatatcta ccaagtcttg ggaagttacc atcacttaag    780
gagctgttta ttcttggcat gagcaaggtg aaagttattg attgggagtt acttggaact    840
ggagttgcat tcccatcact tgaaattcta agttttggtc atatgtcagg gtgggaggta    900
tggtcaaccg agaatagtgg ggttgtagac acagcatttc catgtcttca agaacttcat    960
atcgaatttt gtcctaattt agttcaagtc tcacttgaag ccctaccttc acttagagtt    1020
ttagaaataa aaggatgtgg tcatggtgtg ttgacaactc tggttcatgt agcttcttca    1080
gtcaccatgt tggaaatagg taatatttca gggcttaatg atgaactgtg agaagtgct    1140
ttcaagtatc ttgggaaact tgaaaagtta cattcgtg ggtgtaatga ataagatat    1200
ttgtggcaat cagaagtaga ggcaagtaag tctctagtga atttaaggaa tttggatgtg    1260
agtgattgtt caaatctggt ggggtttagga gagaaagtgg aggataactc tggaagcatc    1320
cagacgttta ttaggatgtt gtctatagca cgttgtgaga ctattgagca ttgcagttgt    1380
cctaatagca ttgagtttct gaatatccat gattgtgatt caattacatc agtgtctttc    1440
ccaaaaggag gagggaagaa gctcaagtca tttgccattg aaggttgtca gaagtttttg    1500
gaagaggagc tcgaggagaa aaagagtagg ttgcttatca actcaaacat gaaaatgctt    1560
gaatctgtag atataaatgg ttgggtaaat ctgaaatcta tcattgaatt gagttactgt    1620
attcacctca ccacattgat gataacaaag tgtccaaaaa tggagtcttt tcctgaccat    1680
gagttaccca atctcacctc tttaacaatt ctgataatag caaagtgtcc aagtattgat    1740
```

-continued

```
gcctcctttc ctcgtgggct ttggcctccc aaattgagtt accttggaat aggaggattg    1800
aagaagccca tctcagagtg gggcccacag aatttcccaa cctcactcga gcacttaatg    1860
ttaaatggcg aatatatga tgatgtgaaa aactttgatc aattgtcgca tcttttcct     1920 tcatctcttg cttctctttc gataacggga tttcagaaac ttgaatcagt ttcattggga    1980
ctccaaaacc tcacctttct ccagcgtctc tctgtttcca agtgcccaaa gatgttacat    2040
ctaccagaaa agttgcttcc ttcgcttttg tctttgagta tcgatagatg cccaaatttg    2100
aataaaagga gcattagaag aagctcctat tggcccctca tctcccttat cccagactct    2160
aggtatgccc ctctcaaagt ttttgacttc ttctag                              2196
```

<210> SEQ ID NO 4
<211> LENGTH: 731
<212> TYPE: PRT
<213> ORGANISM: Lactuca saligna

<400> SEQUENCE: 4

```
Met Pro Val Gly Met Ile Glu Ser Trp Thr Arg Phe Tyr Leu Ser Asn
1               5                   10                  15

Lys Val Leu Asp Asp Leu Leu His Glu Leu Pro Leu Leu Arg Val Leu
            20                  25                  30

Ser Leu Ser His Leu Asn Ile Thr Glu Val Pro Glu Ile Ile Gly Asn
        35                  40                  45

Leu Lys His Leu Arg Tyr Leu Asn Leu Ser His Thr Ser Ile Thr His
    50                  55                  60

Leu Pro Glu Asn Val Cys Asn Leu Tyr Asn Leu Gln Thr Leu Ile Leu
65                  70                  75                  80

Cys Gly Cys Arg Phe Ile Thr Lys Phe Pro Asn Asn Phe Leu Lys Leu
                85                  90                  95

Arg Asn Leu Arg His Leu Asp Ile Ser Asp Thr Pro Gly Leu Lys Lys
            100                 105                 110

Met Ser Ser Gly Ile Gly Glu Leu Lys Asn Leu His Thr Leu Ser Lys
        115                 120                 125

Ile Ile Ile Gly Gly Glu Asn Arg Leu Asn Glu Leu Lys Asn Leu Gln
    130                 135                 140

Asn Leu His Gly Lys Ile Ser Val Trp Gly Leu Gly Asp Val Gln Asn
145                 150                 155                 160

Ala Met Glu Ala Arg Glu Ala Asn Leu Ser Gln Lys Lys Leu Gly Glu
                165                 170                 175

Leu Gln Leu Asp Trp Gly Tyr Gly Asp Tyr Glu Leu Asn Val Ser Arg
            180                 185                 190

Lys Gln Thr His Asp Lys Glu Val Leu Asn Glu Leu Lys Pro Asp Asn
        195                 200                 205

Asp Ser Leu Lys Lys Leu Lys Ile Leu Ser Tyr Gly Gly Thr Glu Phe
    210                 215                 220

Pro Asn Trp Val Gly Ser Pro Ser Phe Leu Met Leu Thr His Val Ser
225                 230                 235                 240

Ile Tyr Phe Cys Glu Glu Cys Thr Tyr Leu Pro Ser Leu Gly Lys Leu
                245                 250                 255

Pro Ser Leu Lys Glu Leu Phe Ile Leu Gly Met Ser Lys Val Lys Val
            260                 265                 270

Ile Asp Trp Glu Leu Leu Gly Thr Gly Val Ala Phe Pro Ser Leu Glu
        275                 280                 285

Ile Leu Ser Phe Gly His Met Ser Gly Trp Glu Val Trp Ser Thr Glu
```

```
                     290                 295                 300
Asn Ser Gly Val Val Asp Thr Ala Phe Pro Cys Leu Gln Glu Leu His
305                 310                 315                 320

Ile Glu Phe Cys Pro Asn Leu Val Gln Val Ser Leu Glu Ala Leu Pro
                325                 330                 335

Ser Leu Arg Val Leu Glu Ile Lys Gly Cys His Gly Val Leu Thr
            340                 345                 350

Thr Leu Val His Val Ala Ser Ser Val Thr Met Leu Glu Ile Gly Asn
            355                 360                 365

Ile Ser Gly Leu Asn Asp Glu Leu Trp Arg Ser Ala Phe Lys Tyr Leu
        370                 375                 380

Gly Lys Leu Glu Lys Leu Tyr Ile Arg Gly Cys Asn Glu Ile Arg Tyr
385                 390                 395                 400

Leu Trp Gln Ser Glu Val Glu Ala Ser Lys Ser Leu Val Asn Leu Arg
                405                 410                 415

Asn Leu Asp Val Ser Asp Cys Ser Asn Leu Val Gly Leu Gly Glu Lys
            420                 425                 430

Val Glu Asp Asn Ser Gly Ser Ile Gln Thr Phe Ile Arg Met Leu Ser
            435                 440                 445

Ile Ala Arg Cys Glu Thr Ile Glu His Cys Ser Cys Pro Asn Ser Ile
        450                 455                 460

Glu Phe Leu Asn Ile His Asp Cys Asp Ser Ile Thr Ser Val Ser Phe
465                 470                 475                 480

Pro Lys Gly Gly Gly Lys Lys Leu Lys Ser Phe Ala Ile Glu Gly Cys
                485                 490                 495

Gln Lys Phe Leu Glu Glu Leu Gly Gly Glu Lys Ser Arg Leu Leu
            500                 505                 510

Ile Asn Ser Asn Met Lys Met Leu Glu Ser Val Asp Ile Asn Gly Trp
        515                 520                 525

Val Asn Leu Lys Ser Ile Ile Glu Leu Ser Tyr Cys Ile His Leu Thr
            530                 535                 540

Thr Leu Met Ile Thr Lys Cys Pro Lys Met Glu Ser Phe Pro Asp His
545                 550                 555                 560

Glu Leu Pro Asn Leu Thr Ser Leu Thr Ile Leu Ile Ala Lys Cys
                565                 570                 575

Pro Ser Ile Asp Ala Ser Phe Pro Arg Gly Leu Trp Pro Pro Lys Leu
            580                 585                 590

Ser Tyr Leu Gly Ile Gly Gly Leu Lys Lys Pro Ile Ser Glu Trp Gly
            595                 600                 605

Pro Gln Asn Phe Pro Thr Ser Leu Glu His Leu Met Leu Asn Gly Gly
    610                 615                 620

Ile Tyr Asp Asp Val Lys Asn Phe Asp Gln Leu Ser His Leu Phe Pro
625                 630                 635                 640

Ser Ser Leu Ala Ser Leu Ser Ile Thr Gly Phe Gln Lys Leu Glu Ser
                645                 650                 655

Val Ser Leu Gly Leu Gln Asn Leu Thr Phe Leu Gln Arg Leu Ser Val
            660                 665                 670

Ser Lys Cys Pro Lys Met Leu His Leu Pro Glu Lys Leu Leu Pro Ser
            675                 680                 685

Leu Leu Ser Leu Ser Ile Asp Arg Cys Pro Asn Leu Asn Lys Arg Ser
        690                 695                 700

Ile Arg Arg Ser Ser Tyr Trp Pro Leu Ile Ser Leu Ile Pro Asp Ser
705                 710                 715                 720
```

```
Arg Tyr Ala Pro Leu Lys Val Phe Asp Phe Phe
            725                 730
```

<210> SEQ ID NO 5
<211> LENGTH: 297
<212> TYPE: DNA
<213> ORGANISM: Artificial Sequence
<220> FEATURE:
<223> OTHER INFORMATION: VIGS Construct 1A

<400> SEQUENCE: 5

```
ttcatgtagc ttcttcagtc accatgttgg aaataggtaa tatttcaggg cttaatgatg    60
aactgtggag aagtgctttc aagtatcttg ggaaacttga aaagttatac attcgtgggt   120
gtaatgaaat aagatatttg tggcaatcag aagtagaggc aagtaagtct ctagtgaatt   180
taaggaattt ggatgtgagt gattgttcaa atctggtggg tttaggagag aaagtggagg   240
ataactctgg aagcatccag acgtttatta ggatgttgtc tatagcacgt tgtgaga      297
```

<210> SEQ ID NO 6
<211> LENGTH: 304
<212> TYPE: DNA
<213> ORGANISM: Artificial Sequence
<220> FEATURE:
<223> OTHER INFORMATION: VIGS Contruct 1B

<400> SEQUENCE: 6

```
tgagttacct tggaatagga ggattgaaga agcccatctc agagtggggc ccacagaatt    60
tcccaacctc actcgagcac ttaatgttaa atggcggaat atatgatgat gtgaaaaact   120
ttgatcaatt gtcgcatctt tttccttcat ctcttgcttc tctttcgata acgggatttc   180
agaaacttga atcagtttca ttgggactcc aaaacctcac ctttctccag cgtctctctg   240
tttccaagtg cccaaagatg ttacatctac cagaaaagtt gcttccttcg cttttgtctt   300
tgag                                                                 304
```

<210> SEQ ID NO 7
<211> LENGTH: 183
<212> TYPE: DNA
<213> ORGANISM: Artificial Sequence
<220> FEATURE:
<223> OTHER INFORMATION: VIGS Construct 2A

<400> SEQUENCE: 7

```
gtggagatca agctggatta taagaaggat ttgtttgatg ggaagaggaa tattgtcacg    60
gcggaggaga tagagagcgg gataaggcgg ctgatggagg atgacgatgt aagagaaaag   120
ataaaagaga tggggaaaaa gagcaaagcg actgttaaag agggaggttc gtcttacgct   180
tct                                                                  183
```

<210> SEQ ID NO 8
<211> LENGTH: 269
<212> TYPE: DNA
<213> ORGANISM: Artificial Sequence
<220> FEATURE:
<223> OTHER INFORMATION: VIGS Construct 2B

<400> SEQUENCE: 8

```
cacattcttg gaattagaaa cacgcccaat cgagtcgttg tctaccgaca gcaggatacc    60
gtctgtgtat ccggtaggac ctgtactgaa cctagaagac ggtgccggaa caccgccgga   120
aagtgacgtc atcagctggt tggacaatca accaccttcc tcggttgttt tcttgtgttt   180
```
tgggagtctg ggatgttttg atgaagtcca agtgaaggag attgcatatg ctttagagcg    240
aagcgggcgt tctttcttgt ggtcactac                                      269

<210> SEQ ID NO 9
<211> LENGTH: 21
<212> TYPE: DNA
<213> ORGANISM: Artificial Sequence
<220> FEATURE:
<223> OTHER INFORMATION: QPCR Forward Primer

<400> SEQUENCE: 9
tccaagtatt gatgcctcct t                                              21

<210> SEQ ID NO 10
<211> LENGTH: 21
<212> TYPE: DNA
<213> ORGANISM: Artificial Sequence
<220> FEATURE:
<223> OTHER INFORMATION: QPCR Reverse Primer

<400> SEQUENCE: 10
cactctgaga tgggcttctt c                                              21

<210> SEQ ID NO 11
<211> LENGTH: 20
<212> TYPE: DNA
<213> ORGANISM: Artificial Sequence
<220> FEATURE:
<223> OTHER INFORMATION: Actin Forward Primer

<400> SEQUENCE: 11
gcgagaaatt gtgcgtgata                                                20

<210> SEQ ID NO 12
<211> LENGTH: 20
<212> TYPE: DNA
<213> ORGANISM: Artificial Sequence
<220> FEATURE:
<223> OTHER INFORMATION: Actin Reverse Primer

<400> SEQUENCE: 12
actcggctgc agtcttcatt                                                20

<210> SEQ ID NO 13
<211> LENGTH: 24
<212> TYPE: DNA
<213> ORGANISM: Artificial Sequence
<220> FEATURE:
<223> OTHER INFORMATION: LsTUA-3 Forward Primer

<400> SEQUENCE: 13
cttcttagtg ttcaatgctg ttgg                                           24

<210> SEQ ID NO 14
<211> LENGTH: 24
<212> TYPE: DNA
<213> ORGANISM: Artificial Sequence
<220> FEATURE:
<223> OTHER INFORMATION: LsTUA-3 Reverse Primer

<400> SEQUENCE: 14
gaagggtaga tagtgaaacc gagc                                           24

<210> SEQ ID NO 15

```
<211> LENGTH: 150
<212> TYPE: PRT
<213> ORGANISM: Lactuca sativa

<400> SEQUENCE: 15

Met Pro Val Gly Met Ile Glu Ser Trp Thr Thr Phe Tyr Leu Ser Asn
1               5                   10                  15

Lys Val Leu Asp Asp Leu Leu His Glu Leu Pro Leu Leu Arg Val Leu
            20                  25                  30

Ser Leu Ser His Leu Ser Ile Lys Glu Val Pro Glu Ile Ile Gly Ser
        35                  40                  45

Leu Lys His Leu Arg Tyr Leu Asn Leu Ser His Thr Thr Ile Thr His
    50                  55                  60

Leu Pro Glu Asn Ile Cys Asn Leu Tyr Asn Leu Gln Thr Leu Ile Leu
65                  70                  75                  80

Cys Gly Cys Cys Phe Ile Thr Lys Phe Pro Asp Asn Phe Leu Lys Leu
                85                  90                  95

Arg Asn Leu Arg His Leu Asp Ile Ser Asp Thr Pro Gly Leu Lys Lys
            100                 105                 110

Met Ser Ser Gly Ile Gly Glu Leu Lys Asn Leu His Thr Leu Ser Lys
        115                 120                 125

Val Ile Ile Gly Gly Glu Asn Arg Leu Asn Glu Leu Lys Asn Leu Gln
    130                 135                 140

Asn Leu His Gly Lys Ile
145                 150

<210> SEQ ID NO 16
<211> LENGTH: 150
<212> TYPE: PRT
<213> ORGANISM: Lactuca sativa

<400> SEQUENCE: 16

Met Pro Val Gly Met Ile Glu Ser Trp Thr Arg Phe Tyr Leu Ser Asn
1               5                   10                  15

Lys Val Leu Asp Asp Leu Leu His Glu Leu Pro Leu Leu Arg Val Leu
            20                  25                  30

Ser Leu Ser His Leu Asn Ile Thr Glu Val Pro Glu Ile Ile Gly Asn
        35                  40                  45

Leu Lys His Leu Arg Tyr Leu Asn Leu Ser His Thr Ser Ile Thr His
    50                  55                  60

Leu Pro Glu Asn Val Cys Asn Leu Tyr Asn Leu Gln Thr Leu Ile Leu
65                  70                  75                  80

Cys Gly Cys Arg Phe Ile Thr Lys Phe Pro Asn Asn Phe Leu Lys Leu
                85                  90                  95

Arg Asn Leu Arg His Leu Asp Ile Ser Asp Thr Pro Gly Leu Lys Lys
            100                 105                 110

Met Ser Ser Gly Ile Gly Glu Leu Lys Asn Leu His Thr Leu Ser Lys
        115                 120                 125

Ile Ile Ile Gly Gly Glu Asn Arg Leu Asn Glu Leu Lys Asn Leu Gln
    130                 135                 140

Asn Leu His Gly Lys Ile
145                 150
```

LETTUCE PLANT RESISTANT TO DOWNY MILDEW AND RESISTANCE GENE

CROSS-REFERENCE TO RELATED APPLICATIONS

This application is the United States national phase of International Application No. PCT/EP2019/083651 filed Dec. 4, 2019, and claims priority to International Application No. PCT/EP2018/085244 filed Dec. 17, 2018, the disclosures of which are hereby incorporated by reference in their entirety.

The Sequence Listing associated with this application is filed in electronic format via Patent Center and is hereby incorporated by reference into the specification in its entirety. The name of the text file containing the Sequence Listing is 2102739_ST25.txt. The size of the text file is 24,657 bytes, and the text file was created on Nov. 27, 2023.

DESCRIPTION

The present invention relates to a lettuce plant that is resistant to downy mildew, more specifically to a lettuce plant that comprises a mutated gene that confers broad spectrum resistance to *Bremia lactucae* in lettuce. Furthermore the present invention relates a resistance gene and a method for obtaining a lettuce plant that is resistant to downy mildew, wherein the method comprises the step of mutating a gene.

Downy mildew refers to several types of oomycete microbes that are parasites of plants. Downy mildew can originate from various species, but mainly of *Peronospora, Plasmopara* and *Bremia*. Downy mildew is a problem in many food crops, in for example in lettuce caused by *Bremia lactucae*, affecting the production of this crop worldwide. Plants that are being affected include food crops such as brassicas (e.g. cabbage), potatoes, grape, spinach, lettuce, onion, tomato, cucumber plants. Downy mildew infection show symptoms of discoloured areas on upper leaf surfaces in combination with white, grey or purple mould located on the other side of the leaf surface below. Disease is spread from plant to plant by airborne spores.

Lettuce, mostly known as *Lactuca sativa*, but also including *Lactuca* species such as *L. serriola, L. saligna* or *L. virosa*, is a very important crop worldwide. Some of the most popular varieties available are Iceberg, Romaine, Butterhead, Batavia and Oakleaf. There are many plant pathogens that affect *L. sativa*, and some of the diseases caused by these pathogens are downy mildew, *Sclerotinia* rot, powdery mildew, *fusarium* wilt of which the most important disease is lettuce downy mildew, which is caused by the *B. lactucae*, an oomycete pathogen that belong to Peronosporaceae.

For some vegetable crops, such as lettuce, cultivars with resistance to downy mildew are available. However, the pathogen under pressure will mutate to break down the disease resistance and new disease resistance in crops is needed to control infection. Especially in lettuce the occurrence of resistant downy mildew is particularly complex as there are many different races, and new resistant downy mildew species emerging all the time.

In lettuce, infection of *B. lactucae* result in yellow to pale green lesions that eventually become necrotic due to secondary pathogens leading to major crop losses. Fungicides can be used to control *B. lactucae*, but eventually *B. lactucae* becomes immune to these chemicals, because over time the pathogen also acquires resistance to fungicides. Furthermore, there are multiple lettuce varieties available that are resistant to *B. lactucae* but resistance is quickly overcome because new *Bremia* races develop rapidly. Therefore, it is of the utmost importance to find other methods to control *B. lactucae* infection. Most preferably is to identify a resistance gene that gives broad resistance against *B. lactucae* and to provide for lettuce plants that are resistant to downy mildew. Therefore, identification of resistance genes is a promising alternative.

Considering the above, there is a need in the art for to provide plants that are resistant to downy mildew and wherein plants have a broad spectrum resistance against this pathogen. Furthermore, it is an object of present invention to provide a method to obtain such downy mildew resistant plants.

SUMMARY

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by a lettuce plant that is resistant to downy mildew, wherein said plant comprises one or more mutations in a SL7 gene, wherein said SL7 gene encodes for a protein sequence of SEQ ID No. 2 or having at least 90% sequence identity with SEQ ID No. 2, preferably at least 95%, more preferably at least 98%, even more preferably at least 99%, most preferably 100%, wherein the one or more mutations in the SL7 gene result in amino acid substitutions on position 38 in the SL7 protein represented by SEQ ID No. 2. Preferably the serine (S) at position 38 in SEQ ID No. 2 is mutated to asparagine (N). The mutated SL7 gene is a dominant resistance gene, and may be homozygous or heterozygous present in a downy mildew resistant lettuce plant.

The majority of disease resistance genes in plants encode nucleotide-binding site leucine-rich repeat proteins, also known as NBS-LRR proteins (encoded by R genes). These proteins are characterized by nucleotide-binding site (NBS) and leucine-rich repeat (LRR) domains as well as variable amino- and carboxy-terminal domains and are involved in the detection of diverse pathogens, including bacteria, viruses, fungi, nematodes, insects and oomycetes. There are two major subfamilies of plant NBS-LRR proteins defined by the Toll/interleukin-1 receptor (TIR) or the coiled-coil (CC) motifs in the amino-terminal domain and are both involved in pathogen recognition.

A leucine-rich repeat (LRR) is a protein structural domain composed of repeating 20 to 30 amino acid stretches that forms an a/l3 horseshoe fold. The domain is rich in the hydrophobic amino acid leucine. The region between the helices and sheets is the protein's hydrophobic core and is tightly sterically packed with leucine residues. On average classical NBS-LLR genes comprise six LRR regions. The SL7 gene is not a classical NBS-LRR gene, since the SL7 protein does not comprise multiple LRR regions, and it does not comprise the NBS domain. The SL7 gene contains only one LRR region, in which the SL7 gene differs from other cases of R genes where multiple LRR regions and the NBS domain are present. It is thought that those domains determine effector recognition and therefore disease susceptibility/resistance. The presence of the SL7 resistance gene will decrease the chances of the pathogen overcoming the resistance, as often seen with the R genes. Even so, combined with R genes, disease resistance (e.g. against downy mildew) may even be further improved.

For the first time a resistance gene has been found in a lettuce plant that is located on chromosome 3 and that can be linked to plant disease resistance. This SL7 gene of present invention gives resistance to *Bremia lactucae* races Bl17 to Bl35, with the exception of Bl16, Bl20, Bl21, Bl23, and Bl27. Preferably, spectrum resistance to *Bremia lactucae* in lettuce comprises resistance to *Bremia lactucae* of at least races Bl17, Bl18, Bl22, Bl24 to Bl26, and Bl28 to Bl35.

To demonstrate that the SL7 gene is related to *Bremia* resistance, this putative resistance gene has been silenced by tobacco rattle virus (TRV)-based virus-induced gene silencing (VIGS) to induce susceptibility to *B. lactucae* infection in resistant *L. saligna* lettuce lines containing the SL7 resistance gene. With VIGS it was demonstrated that the SL7 gene was associated with downy mildew resistance, VIGS gene silencing was used to create *Bremia*-susceptibility in resistant *Lactuca* species. Resistant lettuce plants were transient transformed with an SL7 silencing construct and made susceptible to *B. lactucae* infection, thus by removing the SL7 gene via virus induced gene silencing. According to another preferred embodiment, the present invention relates to the Lettuce plant, wherein the one or more mutations in the SL7 gene result in amino acid substitutions in the region comprised of amino acid positions 6 to 147 in the SL7 protein represented by SEQ ID No.2. The region comprised of amino acids 6 to 147 is an LRR region of SL7, comprising at least one or more LLR domains, preferably at least two, more preferably at least three, most preferably four LLR domains.

According to yet another preferred embodiment, the present invention relates to the Lettuce plant, wherein the one or more mutations in the SL7 gene further result in amino acid substitutions on position 11 in the SL7 protein represented by SEQ ID No.2. Preferably the threonine (T) at position 11 in SEQ ID No. 2 is mutated to arginine (R).

According to another preferred embodiment, the present invention relates to the Lettuce plant, wherein the one or more mutations in the SL7 gene result in amino acid substitutions in the region comprised of amino acid positions 26 to 72 in the SL7 protein represented by SEQ ID No.2. The region comprised of amino acids 26 to 72 is a single LRR domain of SL7.

According to yet another preferred embodiment, the present invention relates to the Lettuce plant, wherein the one or more mutations in the SL7 gene further result in amino acid substitutions on position 40 in the SL7 protein represented by SEQ ID No.2. Preferably the lysine (K) at position 40 in SEQ ID No. 2 is mutated to threonine (T).

According to yet another preferred embodiment, the present invention relates to the Lettuce plant, wherein the one or more mutations in the SL7 gene further result in amino acid substitutions on position 48 in the SL7 protein represented by SEQ ID No.2. Preferably the serine (S) at position 48 in SEQ ID No. 2 is mutated to asparagine (N).

According to yet another preferred embodiment, the present invention relates to the Lettuce plant, wherein the one or more mutations in the SL7 gene further result in amino acid substitutions on position 61 in the SL7 protein represented by SEQ ID No.2. Preferably the threonine (T) at position 61 in SEQ ID No. 2 is mutated to serine (S).

According to yet another preferred embodiment, the present invention relates to the Lettuce plant, wherein the one or more mutations in the SL7 gene further result in amino acid substitutions on position 69 in the SL7 protein represented by SEQ ID No.2. Preferably the isoleucine (I) at position 69 in SEQ ID No. 2 is mutated to valine (V).

According to yet another preferred embodiment, the present invention relates to the Lettuce plant, wherein the one or more mutations in the SL7 gene further result in amino acid substitutions on position 84 in the SL7 protein represented by SEQ ID No.2. Preferably the cysteine (C) at position 84 in SEQ ID No. 2 is mutated to arginine (R).

According to yet another preferred embodiment, the present invention relates to the Lettuce plant, wherein the one or more mutations in the SL7 gene further result in amino acid substitutions on position 91 in the SL7 protein represented by SEQ ID No.2. Preferably the aspartic acid (D) at position 91 in SEQ ID No. 2 is mutated to asparagine (N).

According to yet another preferred embodiment, the present invention relates to the Lettuce plant, wherein the one or more mutations in the SL7 gene further result in amino acid substitutions on position 129 in the SL7 protein represented by SEQ ID No.2. Preferably the valine (V) at position 129 in SEQ ID No. 2 is mutated to isoleucine (I).

According to another preferred embodiment, the present invention relates to the Lettuce plant, wherein the mutations in the SL7 gene result in amino acid substitutions at position 11, 38, 40, 48, 61, 69, 84, 91 and 129 in the SL7 protein represented by SEQ ID No.2. Preferably the mutations are T11R, S38N, K40T, S48N, T61S, I69V, C84R, D91N, and V129I respectively. An SL7 resistance gene of present invention that encodes for the protein that comprises all the above mutations is represented by SEQ ID No. 3 and encodes for the SL7 protein is represented by SEQ ID No. 4.

According to another preferred embodiment, the present invention relates to the Lettuce plant, wherein the mutations in the SL7 gene further result in amino acid substitutions at position 11, 40, and 84 in the SL7 protein represented by SEQ ID No.2. Preferably the mutations are T11R, S38N, K40T, and C84R.

According to another preferred embodiment, the present invention relates to the Lettuce plant, wherein the SL7 gene that comprises one or more mutations and encodes for the protein sequence represented by SEQ ID No. 4. The mutated SL7 gene, being the SL7R gene, is represented by SEQ ID No. 3. Sequencing experiments showed that the protein encoded by the SL7R gene from the resistant plant compared with the protein encoded by the SL7 gene of a plant that is susceptible differs in several amino acids that have been mutated. In particular mutations in the LRR region of the SL7 protein in the amino acid 6 to 147 are of importance to provide resistance to downy mildew, more specifically in the LLR domain of the SL7 protein in the amino acid region of 26 to 72. The downy mildew is caused in the Lettuce plant by an oomycete, more preferably *Bremia lactucae.*

According to yet another preferred embodiment, the present invention relates to the lettuce plant, wherein the plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa.*

According to a preferred embodiment, the present invention relates to the lettuce plant, wherein the mutations in the SL7 gene are obtainable by gene editing techniques, preferably by mutagenesis (e.g. EMS) and/or CRISPR/Cas.

According to another preferred embodiment, the present invention relates to the lettuce plant, wherein the lettuce plant is resistant to downy mildew caused by one or more of *Bremia lactucae* selected from the group of race Bl17, Bl18, Bl22, Bl24 to Bl26, Bl28 to Bl35. A lettuce plant of present invention comprising the SL7 resistance gene is susceptible to downy mildew caused by *Bremia lactucae* Bl16, Bl20, Bl21, Bl23, and Bl27. Preferably, spectrum resistance to *Bremia lactucae* in the lettuce of present invention comprises resistance to *Bremia lactucae* of at least races Bl17, Bl18, Bl22, Bl24 to Bl26, Bl28 to Bl35.

According to yet another preferred embodiment, the present invention relates to the lettuce plant, wherein the resistance gene SL7R of SEQ ID No. 3 is obtainable from deposit number NCIMB 42785.

The present invention, according to a second aspect, relates to seeds produced by the lettuce plant of present invention. The seed comprises the SL7R gene as described above.

The present invention, according to a third aspect, relates to a resistance gene SL7R that confers resistance to *Bremia lactucae* in lettuce plants, wherein the gene comprises a coding sequence of SEQ ID No. 3 or having at least 90% sequence identity with SEQ ID No. 3, preferably at least 95%, more preferably at least 98%, most preferably at least 99%, most preferably 100%. The SL7R gene is a dominant gene. SEQ ID No.3 represents the coding nucleotide sequence of SL7R gene of *Lactuca saligna* and encodes for the SL7R protein sequence represented by SEQ ID No.4. SEQ ID No.4 represents the SL7R protein sequence of *Lactuca saligna* and lettuce plants that express this protein show complete resistance to downy mildew.

According to a preferred embodiment, the present invention relates to resistance gene SL7R, wherein the gene encodes for a SL7R protein that has at least 85% sequence identity with SEQ ID No. 4, preferably at least 90%, more preferably at least 95%, most preferably at least 98%, most preferably 100%.

According to another preferred embodiment, the present invention relates to the resistance gene SL7R, wherein resistance to *Bremia lactucae* in lettuce comprises resistance to *Bremia lactucae* of race Bl17, Bl18, Bl22, Bl24 to Bl26, Bl28 to Bl35. Preferably, spectrum resistance to *Bremia lactucae* in lettuce comprises resistance to *Bremia lactucae* of at least races Bl17, Bl18, Bl22, Bl24 to Bl26, Bl28 to Bl35.

According to yet another preferred embodiment, the present invention relates to the resistance gene SL7R, wherein the plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*.

The present invention, according to a further aspect, relates to a method for obtaining a lettuce plant that is resistant to downy mildew, wherein the method comprises the steps of,
a) crossing a lettuce plant comprised of the resistance gene SL7R of present invention with a lettuce plant that does not comprise said SL7R gene,
b) optionally, selfing the plant obtained in step a) for at least one time,
c) selecting the plants that are resistant to downy mildew.

In the method of present invention the lettuce plant is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*.

The present invention, according to a further aspect, relates to a method for obtaining a lettuce plant that is resistant to downy mildew, wherein the method comprises the step of providing one or more mutations in a SL7 gene of a lettuce plant, resulting in a SL7R resistance gene of present invention. The SL7 gene comprises a coding sequence that has at least 90% sequence identity with SEQ ID No. 1, preferably at least 95%, more preferably at least 98%, most preferably at least 99%, most preferably 100%. SEQ ID No.1 represents the coding nucleotide sequence of the SL7 gene of *Lactuca sativa*. This sequence is the wild type sequence and does not contain the mutations as compared to the resistance gene of present invention.

According to another preferred embodiment, the present invention relates to the method, wherein the one or more mutations in the SL7 gene result in amino acid substitutions in the region comprised of amino acid positions 6 to 147, preferably comprised of amino acid positions 26 to 72, in the SL7 protein represented by SEQ ID No.2. Mutations are located in the LLR region of amino acid positions 6 to 147, preferably in the single LRR domain that is located from amino acid 26 to 72 of the SL7 protein.

According to yet another preferred embodiment, the present invention relates to the method, wherein the one or more mutations in the SL7 gene comprise amino acid substitutions at position 11, 38, 40, and 84 in the SL7 protein represented by SEQ ID No.2.

According to yet another preferred embodiment, the present invention relates to the method, wherein the one or more mutations in the SL7 gene further comprises amino acid substitutions at position 48, 61, 69, 91 and 129 in the SL7 protein represented by SEQ ID No.2.

According to a preferred embodiment, the present invention relates to the method, wherein the SL7 gene that comprises one or more mutations, being the SL7R gene, is represented by SEQ ID No. 3 and encodes for the protein sequence represented by SEQ ID No. 4. SEQ ID No.4 represents the SL7R protein sequence of *Lactuca saligna*. Lettuce, such as *L. sativa* that express the protein of SEQ ID No.4 is resistant to downy mildew.

According to a preferred embodiment, the present invention relates to the method, wherein the mutations in the SL7 gene are obtained by gene editing techniques, preferably by mutagenesis and/or CRISPR/Cas. The lettuce plant comprising the mutations in the SL7 gene is selected from *Lactuca sativa, Lactuca virosa, Lactuca saligna, Lactuca serriola, Lactuca aculeate, Lactuca georgica, Lactuca perennis, Lactuca tatarica, Lactuca viminea*, preferably *Lactuca sativa*. A lettuce plant comprised of the mutations in the SL7 gene gives a high downy mildew resistance phenotype. A plant having this resistant phenotype can be obtained via use of gene editing and/or mutation techniques, such as EMS mutagenesis or CRISPR/Cas in concert with cloning techniques on the SL7 gene to generate disease resistant crops. Mutations induced by gene editing techniques such as mutagenesis, CRISPR/Cas, transgenic techniques, or others can be regarded as non-natural mutations. Alternatively, a SL7R gene can be brought into the plant by means of transgenic techniques or by introgression.

The present invention, according to a further aspect, relates to the use of a gene construct for introducing a resistance gene into the genome of a plant or plant cell, wherein the gene construct is comprised of the resistance gene SL7R of present invention which is operably linked to expression providing sequences in said plant. The resistance gene of present invention may be transferred (e.g. by transformation or transfection) into plants, such as lettuce plants, using a plasmid of vector or linear gene construct that comprises the SL7R resistance gene of present invention or wherein the gene comprises a coding sequence that has at least 90% sequence identity with SEQ ID No. 3. The resistance gene SL7R encodes for a SL7R protein that has at least 85% sequence identity with SEQ ID No. 4. The Resistance gene SL7R, after being transferred into the lettuce plant would provide resistance to *Bremia lactucae* i.e. resistance to *Bremia lactucae* of race Bl17, Bl18, Bl22, Bl24 to Bl26, Bl28 to Bl35.

BRIEF DESCRIPTION OF THE DRAWINGS

The present invention will be further detailed in the following examples and figures wherein:

FIG. 2: shows quantification of *Bremia* actin in Lettuce after VIGS gene silencing. In case SL7R gene expression levels were VIGS silenced in lettuce infected with *Bremia* (Bl30), expression levels of *Bremia* actin increased dramatically. The *Bremia* expression levels in the leaves of plants that showed to be resistant or susceptible to downy mildew after gene silencing, were collected and RNA was isolated to determine the expression levels of *Bremia* by qPCR. The transcription levels of *Bremia lactuca* was determined by the transcripts of a *Bremia* house keeping gene (actin) in relation to the lettuce house keeping gene TUA-3 in a set of leave samples of Lettuce plants of the experiment of FIG. 1. Leaves of the plant that were susceptible to *Bremia lactucae*, showed high transcriptional levels of the *Bremia lactucae* house keeping gene actin, indicating the susceptibility corresponds with low SL7R gene expression due to VIGS silencing.

FIG. 3: shows SL7R expression levels in SL7R VIGS silenced lettuce lines infected with *Bremia* (Bl30), determined by qPCR. The transcription levels of *Bremia lactuca* was determined by the transcripts of a *Bremia* house keeping gene (actin) in relation to the lettuce house keeping gene TUA-3 of *Bremia lactucae* were determined in leave samples of *L. sativa* plants of the experiment of FIG. 1. Leaves of the plants that were resistant to *Bremia lactucae* showed to have a high SL7R gene expression and low transcriptional levels of the *Bremia lactucae* house keeping gene. Leaves of the plant that were susceptible to *Bremia lactucae*, showed low SL7R gene expression (because of VIGS silencing the gene) and high transcriptional levels of the *Bremia lactucae* house keeping gene, indicating the susceptibility corresponds with low SL7R gene expression.

FIG. 4: shows an overview of the disease test performed with the most recent isolates of *Bremia* Bl16 to Bl35 on *L. sativa* lines Cobham Green R273, Green Towers, Vanity and SL7R. SL7R is a lettuce plant (*L. sativa*) of present invention comprising the SL7R resistance gene. The plant of present invention shows to be resistant to most downy mildew isolates, with the exception of *Bremia lactucae* Bl16, Bl20, Bl21, Bl23, and Bl27.

FIG. 5: shows the alignment of the amino acid sequence region of 1 to 150 amino acids, including the LLR region (amino acid 6 to 147) and the single LRR domain (amino acid 26 to 72) of SL7 (SEQ ID No. 15) and the SL7R (SEQ ID No. 16) protein. The mutations between the two protein sequences have been indicated in the boxed areas. The SL7R protein comprises amino acid substitutions at position 11 (T→R), 38 (S→N), 40 (K→T), 48 (S→N), 61 (T→S), 69 (I→V), 84 (C→R), 91 (D→N) and 129 (V→I).

FIG. 6: shows the cDNA sequence (SEQ ID No. 1) encoded by the SL7 gene of *Lactuca sativa*.

FIG. 7: shows the protein sequence (SEQ ID No. 2) encoded by the SL7 gene of *Lactuca sativa*.

FIG. 8: shows the cDNA sequence (SEQ ID No. 3) encoded by the SL7R gene of *Lactuca saligna*.

FIG. 9: shows the protein sequence (SEQ ID No. 4) encoded by the SL7R gene of *Lactuca saligna*.

DETAILED DESCRIPTION

Examples

Gene Mapping SL7 Resistance Gene in *L. saligna*

Gene mapping experiments were done to identify the of the *Bremia* (*Bremia lactucae*) resistance gene SL7R from *Lactuca saligna*. SL7R was originally isolated from *L. saligna* lettuce accession LAC0364. A dominant resistance gene was mapped on chromosome 3, Lettuce genome V8. The SL7R resistance gene is the first *Bremia* resistance gene described and mapped on chromosome 3 in Lettuce.

After fine mapping 12000 plants two putative genes were present. The SL7R region is currently flanked by two markers based on a SNP at position V8_3_200695773 and a SNP at position V8_3_200770104. The two candidate genes are designates as Lsa011563 and Lsa042767. VIGS silencing was used to silence both genes independently in a resistant source (*L. saligna*), see below. These experiments indicated that when resistance gene Lsa011563 was silenced the plants became susceptible after *Bremia* infection, whereas when gene Lsa042767 was silenced, the plants remained resistant. This confirms that the Lsa011563 gene provide the plant resistance against *Bremia*. This resistance gene is renamed to the resistance gene SL7R of present invention.

Construction of SL7 Construct and Transformation into Lettuce (*L. saligna*).

After gene mapping two candidate resistance genes were found and designated as Lsa011563 (=SL7R) and Lsa042767. To identify which gene (or both) are responsible for the observed resistance, VIGS silencing can be used to silence both genes independently in the resistant source *L. saligna*. Therefore, two VIGS-constructs were made per gene, for Lsa011563 (=SL7) (1A and 1B) and for Lsa042767 (2A and 2B) and cloned in the K20 vector (See Table 1 for sequences, respectively SEQ ID No. 5, SEQ ID No. 6, SEQ ID No. 7, SEQ ID No. 8). Thus two SL7R specific VIGS constructs were made (1A and 1B) and two construct that target a different gene Lsa042767 (2A, 2B) can be used as a negative control. The multiple constructs of above were transformed into lettuce (*L. sativa*) using co-cultivation with *agrobacterium* (GV3101) to study the SL7R function. The two resistance candidate genes are individual silenced in VIGS independent experiments. With the leaves of VIGS-experiments independent disease tests (see below) were performed to observe that when SL7R was silenced, plants became susceptible to *Bremia*.

TABLE 1

| VIGS-constructs | Sequence |
|---|---|
| Lsa011563_1A (SEQ ID No. 5) | TTCATGTAGCTTCTTCAGTCACCATGTTGGAAATAGGTAATATT TCAGGGCTTAATGATGAACTGTGGAGAAGTGCTTTCAAGTATCT TGGGAAACTTGAAAAGTTATACATTCGTGGGTGTAATGAAATAA GATATTTGTGGCAATCAGAAGTAGAGGCAAGTAAGTCTCTAGTG AATTTAAGGAATTTGGATGTGAGTGATTGTTCAAATCTGGTGGG TTTAGGAGAGAAAGTGGAGGATAACTCTGGAAGCATCCAGACGT TTATTAGGATGTTGTCTATAGCACGTTGTGAGA |
| Lsa011563_1B (SEQ ID No. 6) | TGAGTTACCTTGGAATAGGAGGATTGAAGAAGCCCATCTCAGAG TGGGGCCCACAGAATTTCCCAACCTCACTCGAGCACTTAATGTT AAATGGCGGAATATATGATGATGTGAAAAACTTTGATCAATTGT CGCATCTTTTTCCTTCATCTCTTGCTTCTCTTTCGATAACGGGA TTTCAGAAACTTGAATCAGTTTCATTGGGACTCCAAAACCTCAC CTTTCTCCAGCGTCTCTCTGTTTCCAAGTGCCCAAAGATGTTAC ATCTACCAGAAAAGTTGCTTCCTTCGCTTTTGTCTTTGAG |
| Lsa042767_2A (SEQ ID No. 7) | GTGGAGATCAAGCTGGATTATAAGAAGGATTTGTTTGATGGGAA GAGGAATATTGTCACGGCGGAGGAGATAGAGAGCGGGATAAGGC GGCTGATGGAGGATGACGATGTAAGAGAAAAGATAAAAGAGATG GGGAAAAAGAGCAAAGCGACTGTTAAAGAGGGAGGTTCGTCTTA CGCTTCT |
| Lsa042767_2B (SEQ ID No. 8) | CACATTCTTGGAATTAGAAACACGCCCAATCGAGTCGTTGTCTA CCGACAGCAGGATACCGTCTGTGTATCCGGTAGGACCTGTACTG AACCTAGAAGACGGTGCCGGAACACCGCCGGAAAGTGACGTCAT CAGCTGGTTGGACAATCAACCACCTTCCTCGGTTGTTTTCTTGT GTTTTGGGAGTCTGGGATGTTTTGATGAAGTCCAAGTGAAGGAG ATTGCATATGCTTTAGAGCGAAGCGGGCGTTCTTTCTTGTGGTC ACTAC |

SL7R Gene Silencing Experiment Using Virus Induced Gene Silencing (VIGS)

Tobacco rattle virus (TRV)-derived VIGS vectors have been abundantly described to study gene function in *Arabidopsis thaliana, Nicotiana benthamiana, Solanum esculentum* and other plants (see for example Huang C, Qian Y, Li Z, Zhou X.: Virus-induced gene silencing and its application in plant functional genomics. Sci China Life Sci. 2012; 55(2):99-108).

Briefly, Lettuce containing SL7 were silenced for SL7R by VIGS. Independent of SL7R silencing the PDS gene is silenced as well that serves as positive control to indicate if VIGS is working and to determine the efficiency. PDS is involved in carotenoid biosynthesis and is the first step in lycopene biosynthesis. This step is catalyzed by phytoene desaturase (PDS). When silencing of the PDS gene is achieved, this results in bleached leaves.

Furthermore, all plants that were SL7R-VIGS inoculated were harvested and put in a tray and sprayed with *Bremia* to test the effect of the gene silencing on disease resistance.

Disease Test and Biotest for Downy Mildew in Lettuce

Leaves of resistant plants transiently transformed with the above described VIGS constructs (1A, 1B, 2A, 2B and PDS), were put in trays with moistened paperboard and infected with *Bremia* race 30. The infected seedlings are suspended in 20 mL water, filtered by cheesecloth and the flow-through is collected in a spray flask. One tray is spray-inoculated with the *Bremia lactucae* suspension. The trays are covered with a glass plate and stored in a climate chamber at 15° C. (12 hours of light). A black, opaque foil is placed over the trays for one day to improve growth of *B. lactucae*. After one day, the foil is removed. Experiments were performed in triple, and eight to ten days after infection leaves are phenotypically scored by eye on the presence of *Bremia*, i.e. being susceptible or resistant (FIG. 1).

Disease resistance tests show that resistance gene SL7R provides resistance to most *Bremia* races from Bl:15 to Bl:35, with the exceptions being Bl:16, BL20, Bl21, Bl23, and Bl:27. Furthermore a qPCR was performed to determine SL7R expression.

A single gene line comprising the SL7R gene used internally to test *Bremia* diagnostic samples is R290. Seeds of this line are deposited at NCIMB (NCIMB Limited, Ferguson Building; Craibstone Estate, Bucksburn ABERDEEN, Scotland, AB21 9YA United Kingdom) on 12 Jul. 2017 under the number NCIMB 42785.

Determine *Bremia* Expression in Lettuce Comprising the SL7R Gene

A number of gene expression experiments were conducted in lettuce tissues obtained from the VIGS experiment as outlined above, to determine SL7R expression. The response of lettuce leaves to *Bremia lactucae* infection was examined and gene expression studies were used to assess VIGS analysis.

To obtain more insight in the response of lettuce to infection with *Bremia*, leaves of resistant and susceptible plants were harvested. cDNA was synthesized from RNA that had been isolated from infected leaves. The expression of SL7R was assessed in lettuce by conducting qPCR. Expression of *Bremia lactucae* actin and expression of SL7R were analyzed by qPCR using the primers as set out in Table 2. (SEQ ID No.9, SEQ ID No.10, SEQ ID No.11, SEQ ID No.12, SEQ ID No.13, and SEQ ID No.14, respectively).

TABLE 2

| Primer name | Sequence |
|---|---|
| SL7QPCR-F | 5'-TCCAAGTATTGATGCCTCCTT-3' (SEQ ID No. 9) |
| SL7QPCR-R | 5'-CACTCTGAGATGGGCTTCTTC-3' SEQ ID No. 10) |
| *B. lactucae* actin Fwd | 5'-GCGAGAAATTGTGCGTGATA-3' (SEQ ID No. 11 |

TABLE 2-continued

| Primer name | Sequence |
|---|---|
| *B. lactucae* actin Rv | 5'-ACTCGGCTGCAGTCTTCATT-3' (SEQ ID No. 12) |
| LsTUA-3F | 5'-CTTCTTAGTGTTCAATGCTGTTGG-3' (SEQ ID No. 13) |
| LsTUA-3R | 5'-GAAGGGTAGATAGTGAAACCGAGC-3' (SEQ ID No. 14) |

Figure 1:
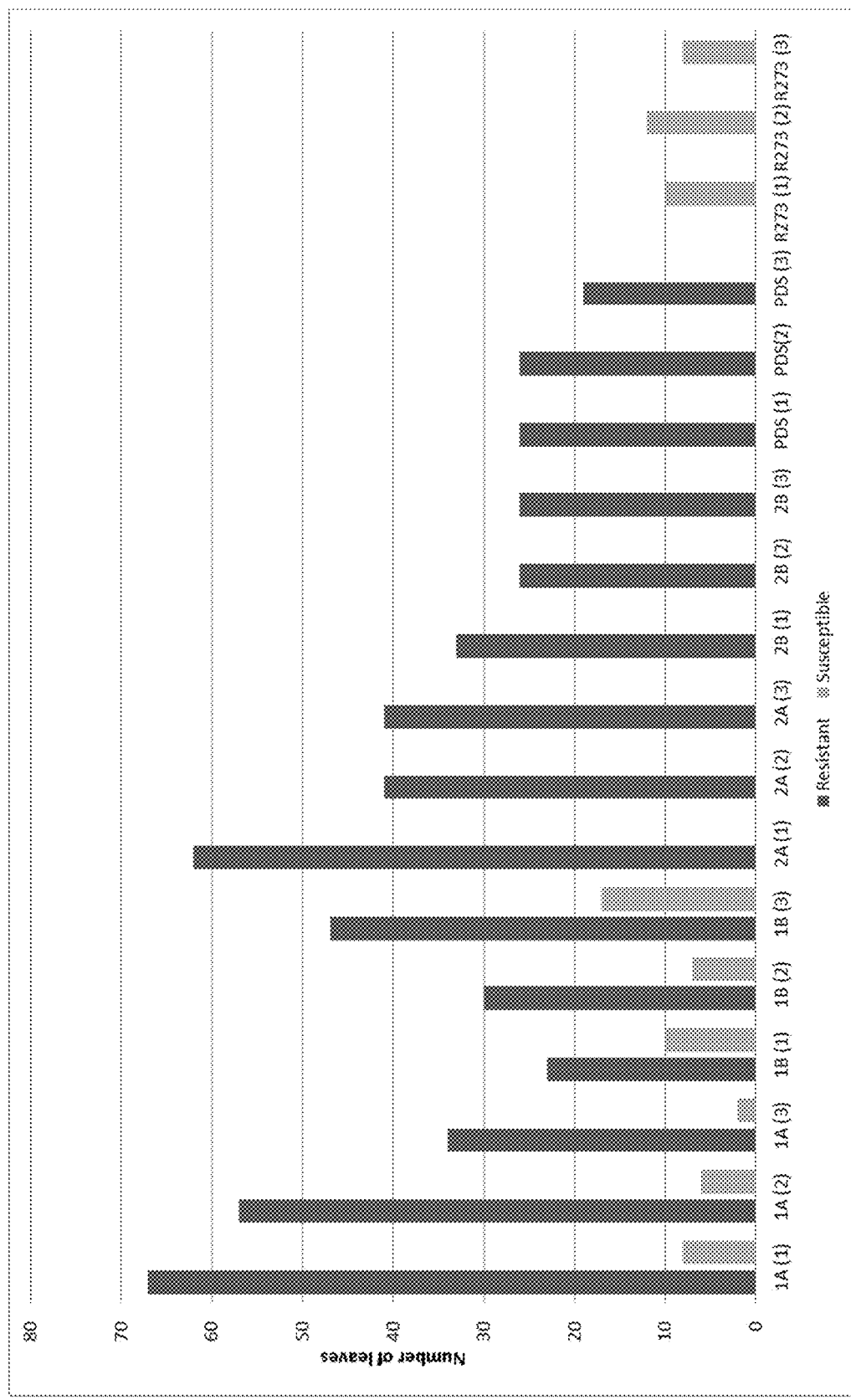
FIG. 1: shows the number (#) of leaves of Lettuce (Y-axis) that are resistant or susceptible to *Bremia lactucae* after VIGS silencing of either SL7R (by 1A and 1B), or gene Lsa042767 (by 2A or 2B) (X-axis). The SL7R gene has been silenced in these plants using VIGS gene silencing and subsequently infected with *Bremia lactucae* (Bl30). On the x-axis from left to right: sample leaves of plants in which the SL7R gene is silenced using silencing construct 1A or 1B, sample leaves of plants in which gene Lsa042767 is silenced using silencing construct 2A or 2B, sample leaves of plants in which PDS is silenced, sample leaves of plants of susceptible parent R273. In the samples with a resistant phenotype, there is no *Bremia* present. In the samples with susceptible phenotypes, *Bremia* is present. As expected with transient gene silencing, VIGS gene silencing does not result in fully 100% silencing of the SL7R gene in all plants. However, the leaves from plants wherein the resistance gene has been silenced by VIGS silencing, showed a higher number of susceptible leaves when infected with *Bremia* as compared to plants where the SL7R gene was not silenced. Indeed no susceptible leaves were observed when SL7R expression was not affected by VIGS.
Figure 2:
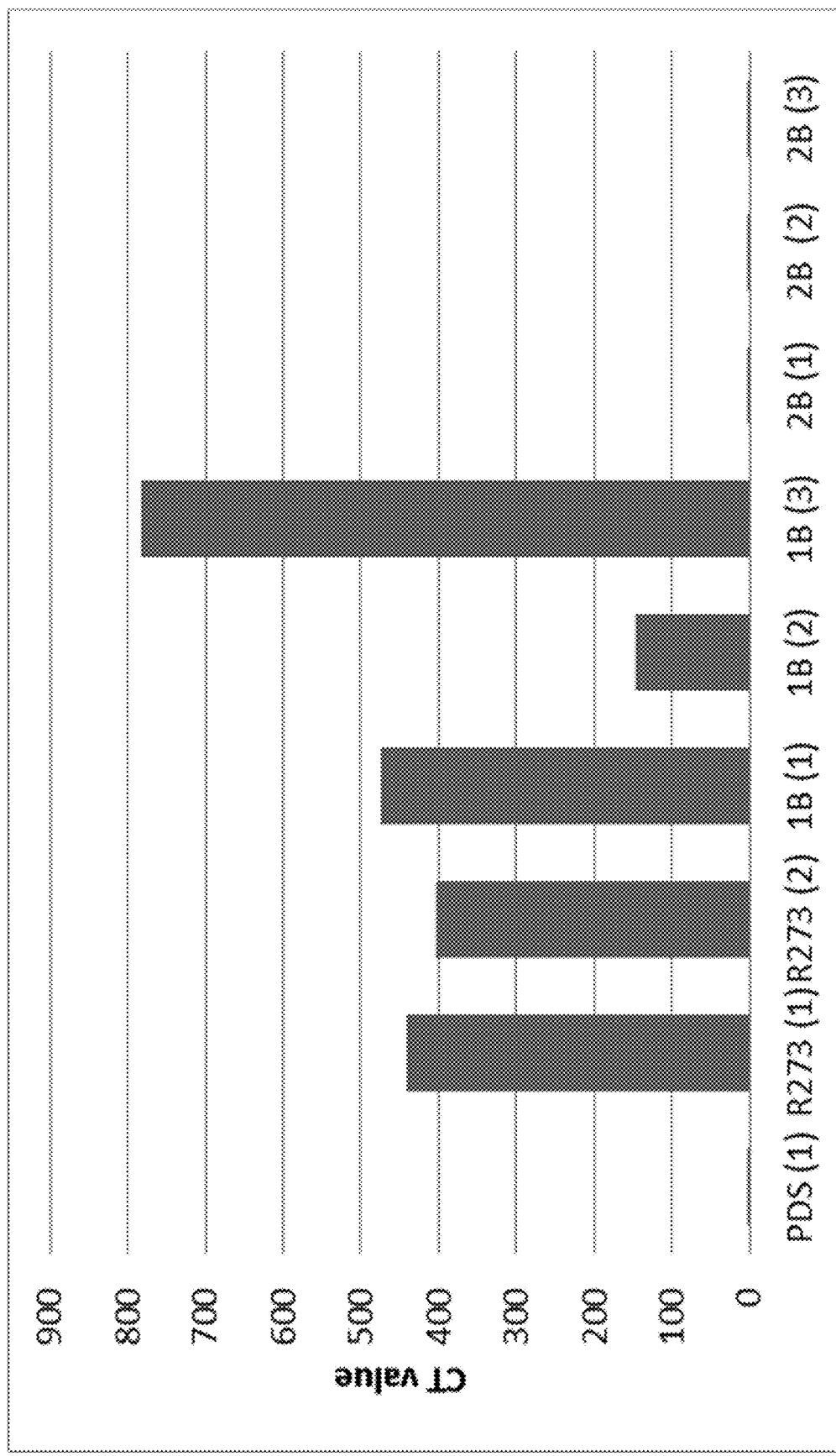

FIG. 2 shows the results of a qPCR of housekeeping gene *Bremia* actin. Values on the y-axis are CT values (the fold increase is calculated as 2^−(Ct *Bremia* actin−Ct TUA3A).

On the x-axis from left to right: sample leaf of a plant in which PDS is silenced, sample leaves of plants of susceptible parent R273, sample leaves of plants in which the SL7R gene is silenced using silencing construct 1B, sample leaves of plants in which the SL7R gene is silenced using silencing construct 2B. In the samples with a resistant (R) phenotype, there is no or almost no *Bremia* present. In the samples with susceptible (S) phenotypes, high transcription levels of the housekeeping gene *Bremia* actin were measured.

Figure 3:
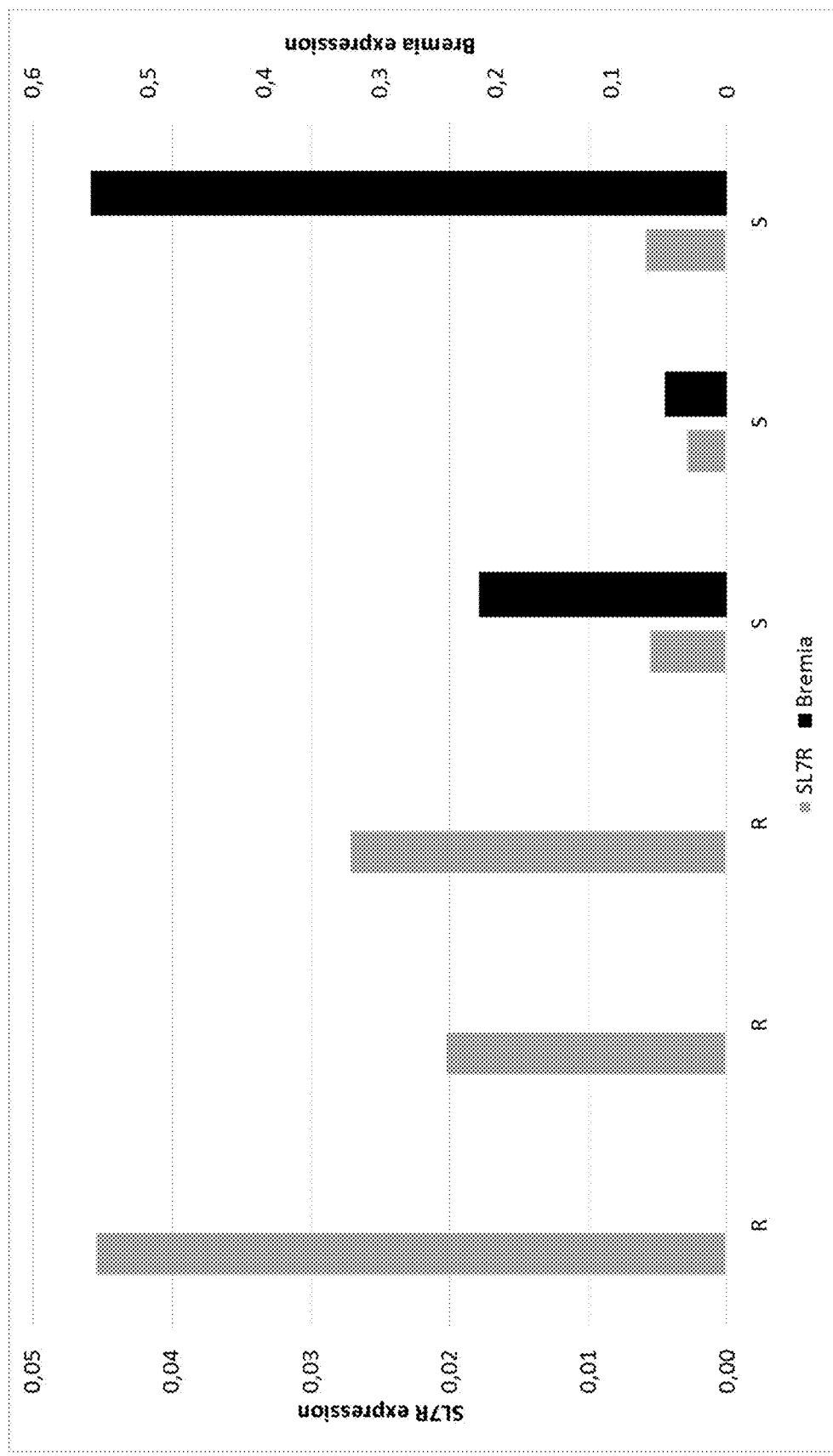

In addition, FIG. 3 shows that in leaves of the plants that are resistant to *Bremia*, little to no *Bremia* was detected and that the level of SL7R expression was very high. The leaves that originate from plants that are susceptible to *Bremia*, showed the opposite pattern, a high level of *Bremia* and low levels of SL7R expression.

The invention claimed is:

1. A *Lactuca sativa* lettuce plant that is resistant to downy mildew caused by one or more of *Bremia lactucae* races B1:16, B1:20, B1:21, B1:23, and B1:27, comprising one or more mutations in a SL7 gene, wherein said SL7 gene encodes for a protein having the sequence of SEQ ID No. 2 or having at least 90% sequence identity with SEQ ID No. 2, wherein the one or more mutations in the SL7 gene comprise amino acid substitutions at positions 11, 38, 40, 48, 61, 69, 84, 91 and 129 corresponding to the SL7 protein sequence SEQ ID NO: 2.

2. The *L. sativa* lettuce plant according to claim 1, wherein the one or more mutations in the SL7 gene comprise a T11R amino acid substitution—at position 11 in the SL7 protein represented by SEQ ID No.2.

3. The *L. sativa* lettuce plant according to claim 1, wherein the one or more mutations in the SL7 gene comprise a K40T amino acid substitution at position 40 in the SL7 protein represented by SEQ ID No.2.

4. The *L. sativa* lettuce plant according to claim 1, wherein the one or more mutations in the SL7 gene comprise a S48N amino acid substitution at position 48 in the SL7 protein represented by SEQ ID No.2.

5. The *L. sativa* lettuce plant according to claim 1, wherein the one or more mutations in the SL7 gene comprise a T61S amino acid substitution at position 61 in the SL7 protein represented by SEQ ID No.2.

6. The *L. sativa* lettuce plant according to claim 1, wherein the one or more mutations in the SL7 gene comprise an I69V amino acid substitution at position 69 in the SL7 protein represented by SEQ ID No.2.

7. The *L. sativa* lettuce plant according to claim 1, wherein the one or more mutations in the SL7 gene comprise a C84R amino acid substitution at position 84 in the SL7 protein represented by SEQ ID No.2.

8. The *L. sativa* lettuce plant according to claim 1, wherein the one or more mutations in the SL7 gene comprise a D91N amino acid substitution at position 91 in the SL7 protein represented by SEQ ID No.2.

9. The *L. sativa* lettuce plant according to claim 1, wherein the one or more mutations in the SL7 gene comprise a V129I amino acid substitution at position 129 in the SL7 protein represented by SEQ ID No.2.

10. The *L. sativa* lettuce plant according to claim 1, wherein the SL7 gene that comprises one or more mutations encodes for a protein having the sequence of SEQ ID No. 4.

11. The *L. sativa* lettuce plant according to claim 1, wherein downy mildew is caused by *Bremia lactucae*.

12. The *L. sativa* lettuce plant according to claim 1, wherein the plant comprises an SL7R gene having the nucleotide sequence of SEQ ID No. 3.

13. Seed produced by a *L. sativa* lettuce plant according to claim 1, wherein the seed comprises the mutant SL7 gene.

14. A method for obtaining a lettuce plant that is resistant to downy mildew caused by one or more of *Bremia lactucae* races Bl:16, Bl:20, Bl:21, Bl:23, and Bl:27, comprising the steps of, a) crossing a first lettuce plant comprising a resistance gene SL7R having the nucleotide sequence of SEQ ID No. 3 with a second lettuce plant that does not comprise said SL7R gene, thereby producing a first offspring plant, wherein the first lettuce plant is selected from *Lactuca virosa, Lactuca serriola, Lactuca aculeate, Lactuca georgica, Lactuca perennis, Lactuca tatarica*, and *Lactuca viminea* and the second lettuce plant is a *L. sativa* lettuce plant;

b) optionally, selfing the first offspring plant obtained in step a) for at least one time, thereby producing a second offspring plant; and c) selecting one or more first and/or second offspring plants that are resistant to downy mildew.

* * * * *

UNITED STATES PATENT AND TRADEMARK OFFICE
CERTIFICATE OF CORRECTION

PATENT NO. : 12,173,303 B2
APPLICATION NO. : 17/414142
DATED : December 24, 2024
INVENTOR(S) : Bas Ter Riet et al.

Page 1 of 1

It is certified that error appears in the above-identified patent and that said Letters Patent is hereby corrected as shown below:

In the Claims

Column 27, Line 67, Claim 1, delete "B1:16, B1:20, B1:21, B1:23, and B1:27," and insert -- Bl:16, Bl:20, Bl:21, Bl:23, and Bl:27, --

Signed and Sealed this
Thirteenth Day of May, 2025

Coke Morgan Stewart
*Acting Director of the United States Patent and Trademark Office*